United States Patent [19]

Husar

[11] 4,341,111

[45] Jul. 27, 1982

[54] PROCESS AND APPARATUS FOR DETERMINING THE VISCO ELASTIC CHARACTERISTICS OF FLUIDS

[75] Inventor: Dieter Husar, Bad Homburg, Fed. Rep. of Germany

[73] Assignee: Fresenius AG, Bad Homburg, Fed. Rep. of Germany

[21] Appl. No.: 127,987

[22] Filed: Mar. 4, 1980

[51] Int. Cl.³ .................. G01N 11/10; G01N 33/48
[52] U.S. Cl. .......................................... 73/64.1; 73/59
[58] Field of Search .................................. 73/64.1, 59

[56] References Cited

U.S. PATENT DOCUMENTS

| | | |
|---|---|---|
| 3,225,588 | 12/1965 | Moulin et al. |
| 3,349,604 | 10/1967 | Banks |
| 3,714,815 | 2/1973 | Hartert ............................... 73/64.1 |
| 3,722,262 | 3/1973 | Gilinson, Jr. et al. ................ 73/59 |
| 3,751,975 | 8/1973 | Katsura ................................. 73/59 |
| 3,943,753 | 3/1976 | Simon |
| 4,026,671 | 5/1977 | Simons et al. |
| 4,045,999 | 9/1977 | Palmer ................................... 73/59 |
| 4,148,216 | 4/1979 | Do et al. ........................ 73/64.1 X |
| 4,154,093 | 5/1979 | Smith et al. |
| 4,202,204 | 5/1980 | Hartert |

FOREIGN PATENT DOCUMENTS

| | | |
|---|---|---|
| 2741060 | 11/1977 | Fed. Rep. of Germany |
| 1558516 | 1/1969 | France ................................. 73/64.1 |
| 2370971 | 6/1978 | France |
| 2402874 | 7/1979 | France |
| 851621 | 10/1960 | United Kingdom |
| 1233881 | 6/1971 | United Kingdom |
| 2004376 | 2/1981 | United Kingdom |
| 507805 | 4/1976 | U.S.S.R. ............................... 73/64.1 |
| 602825 | 4/1978 | U.S.S.R. ............................... 73/64.1 |

OTHER PUBLICATIONS

"Piezoelectric Method of Determining Viscosity at 40 KHZ", W. H. Robinson et al., pp. 1070–1076, Mar. 1978, Journal of Applied Physics, vol. 49, No. 3.

Primary Examiner—Charles A. Ruehl
Assistant Examiner—Joseph W. Roskos
Attorney, Agent, or Firm—Cushman, Darby & Cushman

[57] ABSTRACT

Process and apparatus for determining visco-elastic characteristics of specimens such as fluids and/or of polymerizing mixtures, especially of coagulation fluids such as blood or blood plasma, and their temporal changes by determining the resonance frequency and-/or the amplitude of the resonance frequency of the oscillation system formed by a member and its elastic support which are stimulated for oscillation over a frequency range at least close to the natural or Eigen-frequency of the oscillation system. That member which is so stimulated is either a specimen container or a body therein, the other being fixed, so that there is relative motion between them. The determined resonance frequency amplitude relates to the viscosity of the specimen, while the position of the resonance frequency relates to the elasticity of the specimen and thus to the total elasticicty constant of the oscillation system.

27 Claims, 6 Drawing Figures

PROCESS AND APPARATUS FOR DETERMINING THE VISCO ELASTIC CHARACTERISTICS OF FLUIDS

RELATED CASES

This application is related in general to the copending Hartert application Ser. No. 941,587 filed Sept. 12, 1978, now U.S. Pat. No. 4,202,204 granted May 13, 1980, the contents of which is incorporated hereinto by reference as is the priority document of the present application which is referenced in the attached declaration by the inventor.

PREAMBLE

The invention relates to a process for the determination of the visco elastic characteristics of fluids and/or polymerizing mixtures, especially of coagulation fluids such as blood or blood plasma, and their temporal changes as well as to particularly suitable apparatus for carrying out the process.

A series of so-called global methods of determination, especially for the determination of the coagulation behavior of blood or blood plasma has been known, which follow the temporal course of coagulation and thus make possible disclosures concerning the course and extent of the coagulation and therewith of conclusions regarding characteristics of the blood or blood plasma.

From an essay "Simple, bearable curve drawing coagulation machine for emergency stations, operating rooms and sick rooms" by K. N. V. Kaulla and E. V. Kaulla in the journal "Verh. Dt. Ges. im. Med.", 1977, p. 1183 to 1188 a process has been known for example, in case of which the change of the consistency of blood and blood plasma is determined during the development of the fibrin net. For this purpose, a plunger is submerged in a specimen vessel, which, with an oscillating up and down movement displaces the fluid of blood or plasma specimens and thus subjects it to a flow process. The oscillating movement of the plunger at the same time is exceedingly small in order not to endanger the formation of thin fibrinous threads, by a macroscopically distinct, forced flow process strongly acted upon by pressure. The oscillating drive of the plunger is accomplished by attachment to the diaphragm of a loudspeaker on which a humming tone is produced with a constant frequency of 90 Hz. With increasing viscosity of the fluid specimen, the resistance of the fluid against the oscillating movement of the plunger increases, so that the oscillation amplitude of the loudspeaker diaphragm drops; this increase of the resistance to the forced oscillation of the plunger is determined by a change of the transmit intensity of the current through the loudspeaker.

The main disadvantage of this process consists in the fact that only the change of the resistance opposed to the plunger by the fluid specimen against its oscillation movement enters into the measuring result, afterall, therefore a value dependent jointly on the change of the viscosity and elasticity, tied up inseparably with these two parameters, which thus cannot by itself produce any information about changes of the viscosity or the elasticity. It is furthermore disadvantageous that this value concerning the change of the amplitude of the micro-oscillation is determined, which assumes an extremely sensitive measurement, in order to detect especially the spontaneous start of the change in consistency, since the amplitude is minimal anyway.

In the published German patent application No. P 27 41 060.2-52, which formed the priority basis for the abovementioned U.S. Pat. No. 4,202,204, a process was proposed by which the temporal change of the consistency of a blood specimen is determined in principle by the specimen forming part of an oscillation system stimulated with a constant frequency, the oscillation amplitude of which is changed by a change of the consistency of the specimen, and this change is detected. For this a specimen container is attached at the upper end of an elastic rod, on which orbital oscillation is enforced by stimulation at its lower end, while a locally fixed cylinder dips into the specimen container and the blood specimen. Firstly determined is the resonance frequency of the oscillation system formed by the elastic rod, the specimen vessel and the fluid blood specimen. Then a stimulation frequency is selected which lies barely beside this resonance or natural frequency on that side to which the resonance frequency of the oscillation system shifts while developing an elastic fibrin net in the blood specimen. As a result of that, the stimulation of the oscillation system first takes place outside the resonance frequency, as long as there is no fibrinous formation. As soon as the fibrinous formation starts, the elasticity constant of the oscillation system changes as a result of the increasing elasticity of the fibrin net and shifts its resonance frequency toward the stimulation frequency of the forced oscillation, so that a clear resonance peak occurs in the oscillation. In case of further firming of the fibrin net and thus of a further shifting of the resonance frequency, the latter moves beyond the stimulation frequency of the forced oscillation, so that the tapped amplitude of the oscillation system in case of the shift of the resonance frequency will first rise markedly in the direction of the stimulation frequency and then drop again sharply.

This process, to be sure, achieves an improvement largely independent of troubles as compared to a process, known from the German No. OS 20 19 341, in case of which the fibrin net developing carries along a measuring device dipping into the blood specimen at increasing rotation: the measurement in the area of resonance results in a sharp, clear amplitude peak, which is absolutely recognizable and cannot be superposed by trouble. However, the precision of measurement will suffer in this process from the fact that the occurrence of the resonance peak will not only depend on the actual start of the fibrinous formation, but also on the starting distance between the resonance frequency of the oscillation system and the stimulation frequency; the greater this distance is, the further will the fibrinous development have progressed already before a resonance will occur at all. The distance between the resonance frequency of the oscillation system at the start of measurement and of the stimulation frequency depends, however, on a multiplicity of influences which precisely in case of the small intervals to be aimed at, may cause clearly perceptible changes of this frequency interval.

Moreover, particularly the start of the fibrinous formation is detected by the resonance peak, more or less precisely depending on starting distance to the resonance frequency of the oscillation system, while after over-running the stimulation frequency with the resonance frequency of the oscillation system a strong drop of amplitude occurs in every case, which hardly permits any concrete conclusions for the further course of the fibrinous formation. But precisely by the use of the resonance, this process creates an equivocally determinable criterion of the formation of fibrin and is thus not arranged either as an apparatus technically for the detection of quite minimal changes outside of the resonance.

A very considerable disadvantage of this known process too, consists moreover in the fact that the changes of the elastic state and the changes of viscosity of the fluid specimen are inseparably interconnected on the basis of the measuring principle. A concrete statement concerning the state of viscosity on the one hand and of the elasticity on the other hand cannot be made therefore. Experiments carried out within the scope of this invention have shown, however, that precisely by a separate determination of the viscosity changes on the one hand and of the elasticity changes on the other hand, statements about the important coagulation parameters FI (fibrinogen), FXIII (fibrin-stabilizing factor) and thrombocite number may be qualified in a particularly clear manner.

Thus, the invention is based on the task and starting out from the earlier proposal according to the above-mentioned published German Patent Application No. P 27 41 060.2-52 and its corresponding U.S. Pat. No. 4,202,204 to Hartert, of creating a process, which, for the elimination of disturbing influences on the measurement, makes use of resonance phenomena of an oscillation system comprising the fluid specimen, at the same time however, making possible an exact, separate determination both of the change of elasticity as well as the change of viscosity, and both with regard to the precise start as well as with regard to the further course.

The solution of the task is accomplished by always determining the resonance frequency and/or the amplitude of that frequency.

As a result of the fact that the amplitude is determined in the pertinent resonance frequency, i.e., is always measured, so to speak, in the resonance range of the oscillation system, there will always be available clear and easily recognized measurement values not influenced noticeably by heterodyning disturbances. The frequency position of the resonance frequency in this case clearly represents the course of the determining of the resonance frequency of the oscillation system and thus of the change of the elasticity of the fluid specimen. On the other hand, the amplitude in the resonance frequency is a measure for the progressive damping of the oscillation and thus for the change of the viscosity of the fluid specimen.

Two basic possibilities are available for this: Either the range of the possible position of the resonance frequency is run over with the stimulation frequency ("wobble process") periodically at sufficiently short time intervals, or else the stimulation frequency is set continuously to follow the resonance frequency of the oscillation system and is thus always measured in the resonance frequency. In the first case, and in case of a corresponding recording of the curves per scanning run of the stimulation frequency, there results an amplitude curve containing the resonance peak, whereby however according to the invention the stimulation frequency is not kept constant and determining of the resonance frequency is not waited for, but a set of curves is obtained in correspondingly short temporal intervals through the scanning run of the variable stimulation frequency, which with the start of fibrin formation shows a drop of the amplitude level of the resonance peaks from curve to curve, which corresponds to an increase of the viscosity of the fluid specimen, as well as furthermore a shift of the frequency position of the resonance peak, which corresponds to the shifting of the resonance frequency and thus to the change of the elasticity of the fluid specimen. In the other case, it may be retained say by a trace, in what manner the stimulation frequency had been changed during that time, in order to operate continuously in the resonance frequency, which corresponds to the shifting of the resonance frequency and thus to the change of the elasticity of the fluid specimen, while at the same time and possibly continuously, the amplitude obtained thereby may be scanned, the gradual drop of which corresponds to the increasing damping of the oscillation system and thus to the change of the amplitude of the fluid specimen.

Both possibilities result in an almost delay-free detection of the start of changes of both elasticity as well as the viscosity of the fluid specimen, particularly since the scanning frequency may be kept small enough, according to need, with the stimulation frequency in case of the mentioned possibility, in order to keep time delays during the determination of changes of the resonance amplitude position an amplitude level at the start of the fibrin formation at a value negligible in practice. In both cases, there results in case of need a continuous or quasi-continuous determination of the further course of the elasticity change and of the viscosity change, which permits additional conclusions concerning characteristics of the blood examined.

BRIEF DESCRIPTION OF THE DRAWINGS

Further details, characteristics and advantages of the invention will result from the subsequent description of embodiments on the basis of the drawing.

DETAILED DESCRIPTION

Figure 1:
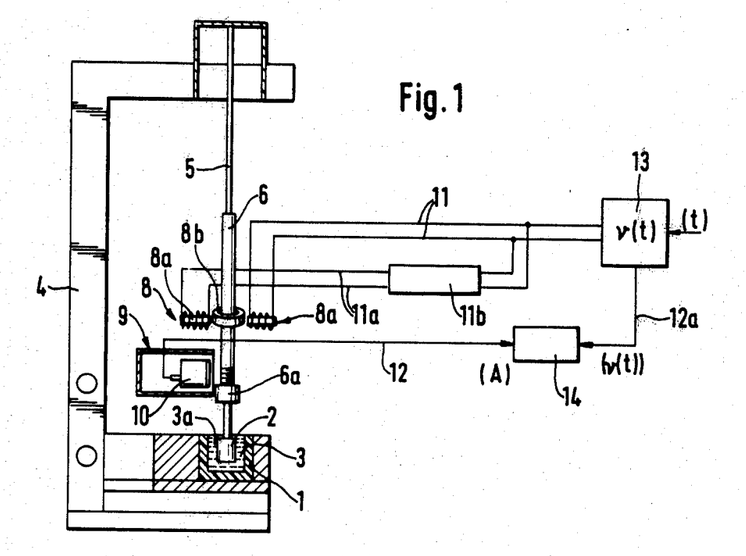
FIG. 1 shows a schematically simplified device for carrying out a first embodiment of the process according to the invention.
Figure 2:
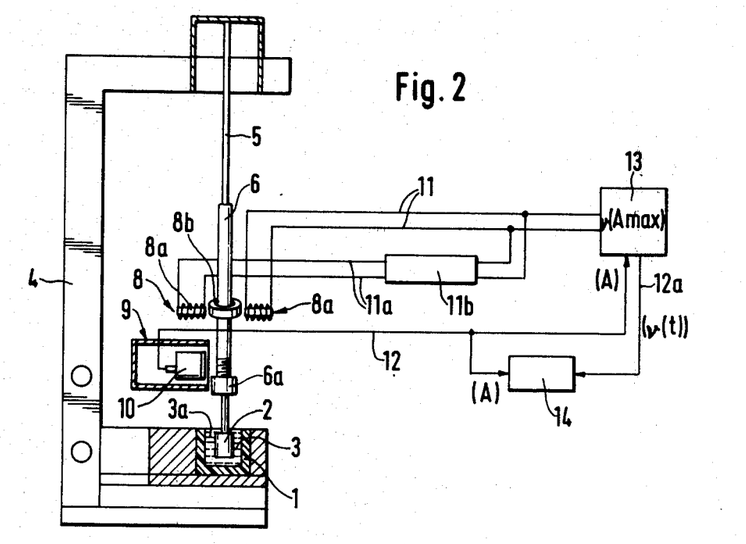
FIG. 2 is a presentation corresponding to FIG. 1 and shows a device suitable for carrying out a second embodiment of the process according to the invention.

FIGS. 1 and 2 show a possible basic construction of a device for carrying out the process of the invention, wherein similar parts are given the same reference numbers. Specimen container 1 is a developed hollow cylinder in the example and with which a cylindrical body 2 engages in such a way that a space 3 remains between the outside wall of body 2 and the inside wall of specimen container 1, in which a fluid specimen 3a, for example, a small quantity of blood, is located. At the same time the body 2 is completely submerged in the fluid specimen 3a. The size of the space 3 between body 2 and the inside wall of specimen container 1 is not critical as long as no impediment occurs of the relative oscillating movement between specimen container 1 and body 2, and may be selected as large as long as practicable measurements of the specimen container are not exceeded thereby. The specimen container 1 and the body 2 may be made easily exchangeable and in case of production from a cheap working material such as a suitable plastic may be discarded after each measurement, or else they may consist of a durable working material such as, say, V2A-steel and be cleaned after every measurement. The specimen container 1 may furthermore be stored with more specimen containers on a gliding or slideable holder, which is shifted in rhythm after every measurement vis-a-vis the body 2 in such a way that said body 2, possibly after having been exchanged, submerges into a new specimen container 1. As known from multiple cuvettes, such a multiple arrangement may also be developed as a rotary plate, sliding rail, etc. Beside the rationalization effect concerning the measuring process, such a multiple arrangement also produces a simple possibility for the attachment of a temperature control device, which always keeps the temperature in the specimen containers 1 at body temperature. Naturally, such a temperature control device may also be used in case of individual specimen containers 1. Since such temperature control devices are known per se, any further discussions of them is superfluous.

In the example, the specimen container 1 is disposed firmly on the device frame 4, which may suitable be foldable, while body 2 is suspended from an elastic member 5. Basically, the specimen container 1 could also be attached to member 5 at its upper end, while the body 2 is held firmly on the frame, but in this case, the use of exchangeable specimen containers 1 and of bodies 2 causes greater difficulties. In every case, the body 2 is moveable vis-a-vis the specimen container 1 because of the elastically bending development of the support either of the body 2 or of the specimen container 1—in case of the example of the member 5—whereby in case of an oscillation stimulation a relative oscillation may take place of the part not fixed in the frame—specimen container 1 or body 2—while acting on the fluid sample 3a. In order to adjust to a suitable resonance frequency, the member 5 is provided with a thickening 6 nearer its free end, or with a corresponding cuff as well as an adjusting weight 6a, for example, adjustable in height by a screw thread.

Provided preferably on the half of its longitudinal extent adjacent to the free end of the member 5 is an oscillator drive 8, which in the example, consists of four electromagnets 8a disposed mutually perpendicularly for the production of an orbital oscillation, and upon energization attract and repulse member 5 by acting in a suitable manner on the iron containing material of member 5 or, in the example, on the annular magnet 8b which is attached, say, by adhesion to member 5. For the sake of simplification of the illustration, only two mutually opposite electromagnets 8a are shown in the drawing, as required for the production of a translatory oscillation in one plane; an orbital oscillation may be produced particularly simple possibly by only two electromagnets 8a which then, however, lie at a mutual angle of 90°.

As close as possible to the free end of member 5, where the oscillation deflections are greatest, an amplitude or oscillation sensor 10, for example in the form of a Hall generator, etc., is disposed to respond upon approach of the adjacent section of member 5. The oscillation sensor 10 is mounted in the example for the sake of comparison closely adjacent to the electromagnets 8a, disposed preferably likewise near the free end of member 5 and is surrounded by a housing-like screening 9 of the magnetic field, which serves as a protection against actions from the direction of the electromagnets 8a. In case of oscillations of the member 5 with a component in the direction of the oscillation sensor 10, the latter detects the approach and removal of the member 5 and delivers to measuring line 12 a signal proportional to the distance corresponding to the momentary distance of member 5.

The details of construction of the device shown merely serve for the illustration of a possible, preferred embodiment, of which many variations are possible. Thus, for example, the reduction of the oscillation amplitude may take place also in any other suitable manner instead of by way of a Hall generator as oscillation sensor 10, whereby however a reduction of the amplitude free of contact is preferred in order not, or in any case not essentially, to impede the free oscillation of the body 2 by reactions to the recording of the measured value.

A corresponding mechanical drive, as apparent for example, from the German Pat. No. OS 20 19 341, which because of some more details will be referred to especially, may be used instead of the electromagnetic oscillation drive 8. Furthermore, it is not absolutely necessary to force an orbital movement on member 5, but a linear oscillation movement may also be used. Correspondingly, the specimen container 1 and body 2 need not be developed as a hollow cylinder or cylindrically. Furthermore, space 3 may also be correspondingly developed deviating from the annular form, say be flat, and may be transverse to the direction of oscillation or in any case enclose a finite angle with the latter. Also, it is not absolutely necessary to adapt the inside wall of the specimen container 1 to the form of the outside wall of the body 2, as long as deviations are compensated by a sufficiently wide interval 3. In case of an orbital movement, member 5 or a section of the member resulting in the elasticity is developed preferably with a round cross section, and therefore shows in any case the same elasticity in both axes of the orbital movement; in case of a linear oscillation movement, member 5 may also be developed as a flat spring leaf or contain such in one sector or be connected to one. The development of the mounting of member 5 is likewise open to choice and depends on its development in its detail as well as on the kind of the forced oscillation.

In case of an electromagnetic oscillation drive 8, action on the current of the electromagnet 8a takes place via lines 11 from a control part 13. The control part 13 controls the through-flow of the current through the coils of the electromagnets 8a, whereby a direct control takes place via the lines 11 only on one electromagnet 8a, while the remaining electromagnets 8a, as illustrated in the drawing for one electromagnet, are triggered via branch lines 11a and always one phase-shifter 11b in such a way that always one correspondingly phase-shifted triggering of the additional electromagnets 8a takes place, independently of the speed of the triggering via the main lines 11, in such a way that a clean oscillation stimulation is assured.

Essential for carrying out the process of the invention is the fact that the fluid specimen 3a is acted upon by the wall of a swinging body, which is part of an oscillation system with definite resonance frequency, which as a result of reactions from the fluid, depends on the elasticity features of the fluid. In principle, as in the embodiment of the example, the elastically mounted body 2 may be driven thereby, or else the rigidly mounted specimen vessel, so that it will carry along (drive) the elastically mounted body 2 via the fluid specimen 3a, and thus stimulates it to corresponding oscillations. In any case, the visco-elastic fluid 3a acts within the area of an oscillation bulge of a stimulated oscillation, corresponding to its elasticity characteristics as a spring support and corresponding to its viscosity characteristics as a damping member on the oscillation system. In case of changes of the elasticity characteristics of the visco-elastic fluid 3a, there thus results a change of the Eigen-frequency of the oscillating system, therefore a change of its overall elasticity constant, whereas in case of changes of the viscosity of fluid 3a, a change of the damping of the oscillation system results.

The orbital pendulum movement of the moving member 5 takes place such that the amplitude forced by it lies in the resonance in a range of 1 to 100 microns ($\mu$m), preferably of 10 to 50 $\mu$m. Whenever the amplitude becomes greater, then there is a danger that the fibrin net can no longer participate in the elastic oscillation and snaps or is torn within itself. On the other hand, the amplitudes in the resonance below 1 $\mu$m are too small in order to be able to measure the effects produced at a reasonable expenditure for measuring.

Figure 6:
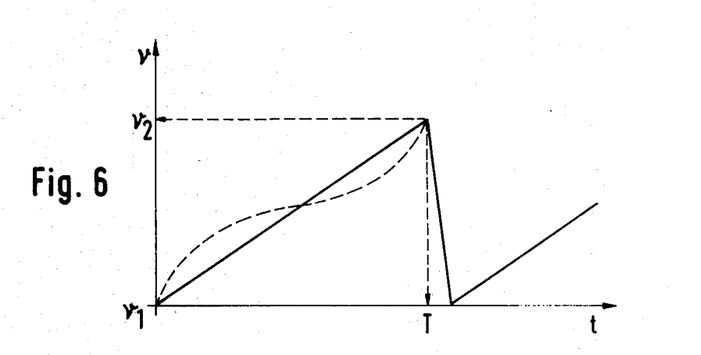
FIG. 6 shows an exemplified course of the scanning in case of the first embodiment of the invention.

In case of the arrangement as in FIG. 1, the control part 13 adjusts the stimulation frequency of the oscillation drive 8, depending on time t, in a predetermined manner. For this purpose a flip-flop circuit may be provided for example in the control part 13 which results in a sawtooth-like course of the stimulation frequency between a lower frequency $\nu_1$ and a higher frequency $\nu_2$ in the manner apparent from FIG. 6; at the same time the frequency course does not need to be linear, as shown in FIG. 6 in solid lines, but some deviating course, for example according to the broken lines in FIG. 6 is also possible, so that perhaps a controlled, amplitude-antiproportional frequency course may be set, so that the scanning in the resonance is particularly slowly variable, which may be of advantage in case of non-linear oscillation behavior of the fluid specimen. In the time period T, which is needed for passing through the frequency scanning range between $\nu_1$ and $\nu_2$, and which typically in the case of blood as fluid 3a may lie between about 0.2 and 200 seconds, if a predetermined frequency range is exceeded the frequency is returned quickly to the starting frequency of the scanning range and the scanning is started again. Naturally, the scanning at the same time may be guided from the lower frequency to the higher frequency of the scanning range or vice versa, and instead of a quick return to the starting frequency, a running over of the scanning range in the opposite direction may take place while carrying out a practical scanning.

The frequency range of the scanning between $\nu_1$ and $\nu_2$ is selected such in every case, that the pertinent resonance frequency of the oscillation system formed by member 5 and body 2 is assuredly over run, i.e., encompassed. For this purpose the frequency range of the scanning may lie effectively between about at 0.1 times and 3 times of the starting resonance frequency of the oscillation system, but in order to avoid superfluous dead-times, advantageously a frequency range of the scanning between 0.8 times and 1.8 times the starting resonance frequency is selected, whereby consideration is to be given to the fact that in case of a coagulation of the fluid 3a formed by blood, the elasticity constant of the oscillation system becomes harder as a result of the development of the fibrin web and thus the resonance frequency rises. In case of a starting resonance frequency of the oscillation system of for example, 80 Hz, the scanning frequency range or "wobble" range may be selected between $\nu_1=65$ and $\nu_2=140$ H3.

Figure 3:
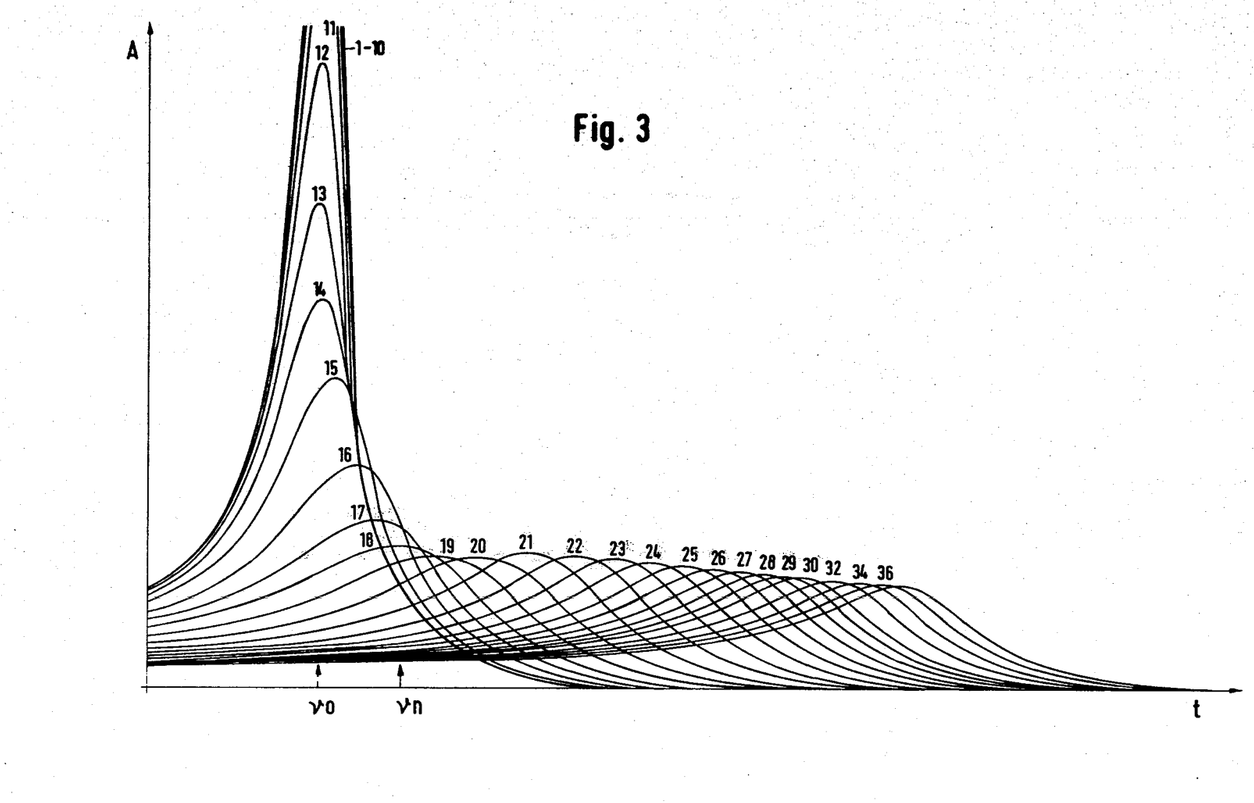
FIG. 3 shows a set of curves, obtaining in case of the first embodiment of the process according to the invention by way of example, for the illustration of the results of measuring.

Amplitude curves determined in case of such scanning, as detected on the oscillation sensor 10 are shown in FIG. 3. An illustration of the amplitude curves favorable for their use may be achieved according to FIG. 3 through the fact that an x-y recorder 14 is connected to line 12 and a line 12a from the direction of the control part 13 for assignment of the pertinent stimulation frequency, the abscissa pencil of which runs with the time and its ordinate pencil with the pertinent amplitude, whereby in the beginning of each scanning in one scanning direction, the abscissa recorder has again moved back to zero in order to record the successive scanning curves above a specific scanning time scale. Since the assignment of the stimulation frequency in the course of scanning is predetermined in relation to the time in the control part 13, for example, linearly according to the solid line in FIG. 6, a certain stimulation frequency may thus be assigned to every point in time on the abscissa of the recorder, namely that stimulation frequency which the control part 13 has reached after a predetermined time from the beginning with the scanning. Thus, the abscissa is at the same time a measure for the pertinent stimulation frequency.

As is clear from FIG. 3, the first scanning curves in the course of measurement overlap; in the case of the example, the curves of the first to the tenth scanning. This shows, that during the corresponding scanning time no parameter of the oscillation system was subjected to change, so that resonance with essentially the same amplitude results always in case of the same stimulation frequency, corresponding to the starting Eigenfrequency of the oscillation system. A first change is to be found between the tenth scanning curve and the eleventh scanning curve. Since the resonance amplitude no longer reaches the original height, this permits a conclusion of increased damping becoming effective. The subsequent curves show an amplitude level rising steeply at first then dropping down flat, which corresponds to the course of damping by raising the viscosity of the specimen fluid. Simultaneously it was found that the position of the amplitude maximum according to FIG. 3 shifts increasingly to the right, thus it occurs later and later in the scanning cycle, which may be assigned to an occurrence in case of correspondingly higher frequency. In FIG. 3, $\gamma_0$ illustrates the position of the starting resonance frequency of the oscillation system and $\gamma_n$ in the example, the position of the Eigenfrequency of the oscillation system at the time of the recording of the eighteenth scanning, as a result of which the shifting of the resonance frequency clearly results. This shifting of the resonance frequency has its cause in a change of the elasticity of the fluid 3a and thus in the total elasticity constant of the oscillation system.

In this manner, changes both of the viscous as well as of the elastic characteristics of the visco-elastic fluid 3a may be determined separately concerning the start and the course of the change. Naturally, according to the control of the control part 13, and in dependence on the time t, the point in time counted from the start of scanning also is fixed, at which every single scanning curve was recorded, so that the course of the change of the resonance frequency of the oscillation system above the time as in FIG. 4 and the course of the change of the maximal amplitude height in case of the resonance according to FIG. 5, may be determined from the information contained in FIG. 3. Instead of a determination of the curves according to FIGS. 4 and 5 from the measurement point which may be read from FIG. 3, a computational processing of the measured values according to FIG. 3 is naturally also possible in a manner known per se, which leads directly to the curves of FIGS. 4 and 5. Beyond that, FIG. 3 still contains additional detailed information corresponding to the precise course of the amplitude in case of every single scanning, from which possibly further knowledge of details of the course of the changes in consistency in the fluid specimen 3a may be deduced and conclusion for the factors on which these changes are based may be drawn.

Figure 4:
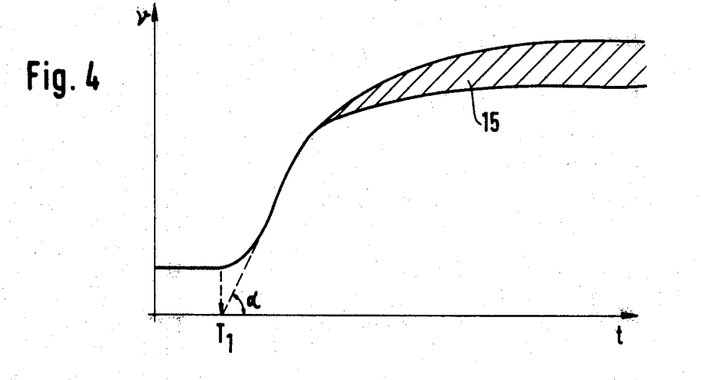
FIGS. 4 and 5 are measuring curves of standard blood for the change of the resonance frequency or of the amplitude as may be obtained with the second embodiment of the invention directly and with the first embodiment of the invention indirectly.
Figure 5:
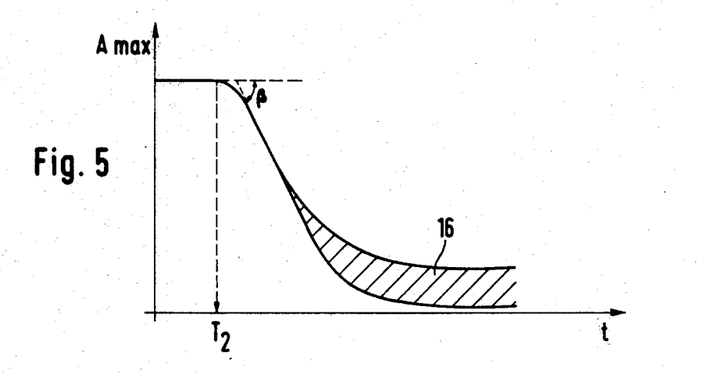

With an arrangement as in FIG. 2, the measurement curves as in FIGS. 4 and 5 may also be obtained directly. A control part 13 has been provided for this purpose, which produces an automatic secondary control of the stimulation frequency of the oscillation drive 8 on the momentary resonance frequency of the oscillation system. The amplitude found by the oscillation sensor 10 is guided for this purpose to the control part 13 as an actual value, which readjusts the stimulation frequency continuously in such a way that the momentary value of the amplitude becomes a maximum. This means that the resonance amplitude is always—in case of need, also intermittently—scanned by the oscillation sensor 10, so that so-to-speak the maximal amplitude of the curves shown in FIG. 3 is always present. Thus, according to FIG. 5, the course of the maximal resonance amplitude over the time results in the decrease which corresponds to the damping. Through formation of the inversion value of the maximal amplitude as in FIG. 5, naturally the damping, which rises correspondingly, may also be recorded, which is a direct measure for the viscosity of the specimen fluid 3a. At the same time it will be possible to record on lines 12a above the time—in case of the example above, the same time abscissa of the joint x-y recorder 14—which stimulation frequency the control part 13 adjusts at any time, which corresponds to the course of the resonance frequency of the oscillation system of FIG. 4, since the stimulation frequency is indeed adjusted always to the resonance frequency of the oscillation system. In this way, the curves of FIGS. 4 and 5 always result directly from the measuring arrangement and may be recorded for example on two different or one common recorder, so that in this way the start and course of the changes of the elasticity are likewise determined separately from changes of viscosity. In FIGS. 4 and 5, areas 15 and 16 are shown in broken lines in the coasting range of the measuring curves, inside of which lies the course of the curve in case of one oscillation in normal blood. In the temporally preceding range, as precise as possible values for the time $T_1$ of the start of the change of the elasticity module of the specimen fluid 3a and for the time $T_2$ of the start of the change of the viscosity of the specimen fluid 3a as well as for the rise $\alpha$ of the elasticity module and the rise $\beta$ of the damping (corresponding to the drop of the amplitude) may be determined from the measurement curves.

Thus, depending on the pertinent requirements of the measurement, it will be possible with the process of the invention to obtain in the individual case a family of curves as in FIG. 3 or a curve development as in FIGS. 4 and 5, so that all relevant changes of the visco-elastic behavior of the specimen fluid 3a may be determined quickly and securely separate of one another.

What is claimed:

1. In a process for determining the visco-elastic properties of specimens including fluids and/or a polymerizing mixture, especially of coagulating fluids such as blood or blood plasma, and their temporal changes, using an elastic oscillation system including said specimen, the natural resonant frequency of said system changing as said specimen properties change,
the improvement characterized by:
monitoring at least the changing frequency position of the resonant frequency of said oscillation system occurring as said specimen properties change for determining specimen elasticity changes.

2. In a process for determining the visco-elastic properties of specimens including fluids and/or a polymerizing mixture, especially of coagulating fluids such as blood or blood plasma, and their temporal changes, using an elastic oscillation system including said specimen, the natural resonant frequency of said system changing as said specimen properties change,
the improvement characterized by:
detecting changes in the amplitude of the resonant frequency of said oscillation system as said specimen properties change, and
using said amplitude changes for developing a readout of at least the changing frequency position of the resonant frequency of said oscillation system for determining specimen elasticity changes.

3. In a process for determining the visco-elastic properties of specimens including fluids and/or a polymerizing mixture, especially of coagulating fluids such as blood or blood plasma, and their temporal changes, using an elastic oscillation system including said specimen, the natural resonant frequency of said system changing as said specimen properties change,
the improvement characterized by:
reading out changes in the amplitude of the resonant frequency of said oscillation system as said specimen properties change, and
simultaneously indicating the changing frequency position of the resonant frequency of said oscillation system occurring as said specimen properties change for determining specimen elasticity changes.

4. In a process for determining the visco-elastic properties of specimens including fluids such as blood or blood plasma, and their temporal changes, using an elastic oscillation system including said specimen, the natural resonant frequency of said system changing as said specimen properties change,
the improvement characterized by:
stimulating said elastic oscillation system into oscillation by applying an excitation signal continually varying in frequency so as to coincide at least momentarily with successive momentary resonant frequencies of said oscillation system resulting from said specimen property changes, and monitoring at least the changing frequency position of the resonant frequency of said oscillation system occurring as said specimen properties change for determining specimen elasticity changes.

5. In a process for determining the visco-elastic properties of specimens including fluids and/or a polymerizing mixture, especially of coagulating fluids such as blood or blood plasma, and their temporal changes, using an elastic oscillation system including said specimen, the natural resonant frequency of said system changing as said specimen properties change, the improvement characterized by:
stimulating said elastic oscillation system into oscillation by applying an excitation signal varying in frequency so as to coincide at least momentarily with successive momentary resonant frequencies of said oscillation system resulting from said specimen property changes,
monitoring changes in the amplitude of the resonant frequency of said oscillation system as said specimen properties change, and
simultaneously monitoring the changing frequency position of the resonant frequency of said oscillation system as said specimen properties change for determining specimen elasticity changes.

6. In a process for determining the visco-elastic properties of specimens including fluids and/or a polymerizing mixture, especially of coagulating fluids such as blood or blood plasma, and their temporal changes, using an elastic oscillation system including said specimen, the natural resonant frequency of said system changing as said specimen properties change, the improvement characterized by:
stimulating said elastic oscillation system into oscillation by applying thereto an excitation signal varying in frequency so as to coincide at least momentarily with successive momentary resonant frequencies of said oscillation system resulting from said specimen property changes,
detecting changes in the amplitude of the resonant frequency of said oscillation system as said specimen properties change, and
monitoring at least the changing frequency position of the resonant frequency of said oscillation system occurring as said specimen properties change for determining specimen elasticity changes.

7. In a process for determining the visco-elastic properties of specimens including fluids and/or a polymerizing mixture, especially of coagulating fluids such as blood or blood plasma, and their temporal changes, using an elastic oscillation system including said specimen, the natural resonant frequency of said system changing as said specimen properties change, the improvement characterized by:
stimulating said elastic oscillation system into oscillation by applying an excitation signal varying in frequency so as to coincide at least momentarily with successive momentary resonant frequencies of said oscillation system resulting from specimen property changes,
detecting changes in the amplitude of the resonant frequency of said oscillation system as said specimen properties change, and
using said amplitude changes for developing an indication of the changing frequency position of the resonant frequency of said oscillation system for determining specimen elasticity changes.

8. In a process for determining the visco-elastic properties of specimens including fluids and/or a polymerizing mixture, especially of coagulating fluids such as blood or blood plasma, and their temporal changes, using an elastic oscillation system including said specimen, the natural resonant frequency of said system changing as said specimen properties change, the improvement characterized by:
detecting changes in the amplitude of the resonant frequency of said oscillation system as said specimen properties change, and
monitoring at least the changing frequency position of the resonant frequency of said oscillation system occurring as said specimen properties change for determining specimen elasticity changes.

9. Process as in claim 8, 2, 3, 5, 6, or 7, characterized in that the determination of the amplitude is carried out exclusive in the resonance frequency of the oscillating system.

10. Process as in claim 4, 5, 6, or 7, characterized in that the stimulation frequency is readjusted at least quasi-continuously in relation to the resonance frequency of the oscillation system.

11. Process as in claim 10, characterized in that the required readjustment change of the stimulation frequency or of a measurement value derived therefrom, is recorded additionally to the pertinent amplitude as a function of time.

12. Process as in claim 10 characterized in that the stimulation frequency overruns the resonance frequency range of the oscillation system for scanning in short time intervals as against the speed of the temporal change of the visco-elastic characteristics to be measured.

13. Process as in claim 12, characterized in that the scanning is carried out with predetermined change of the stimulation frequency.

14. Process as in claim 13 characterized in that the scanning curves are recorded over time at the beginning of each scanning run superposed on one another.

15. Process as in claim 12 characterized in that the scanning frequency in case of blood or blood plasma as fluid is selected between about 2 and 0.005 Hz.

16. Process as in claim 12 characterized in that the frequency range of the scanning is selected between 0.1-fold and 3-fold, preferably between about 0.8-fold and 1.8-fold, of the starting resonance frequency of the oscillation system.

17. Process as in claim 4, 5, 6, or 7, characterized in that the starting resonance frequency of the oscillation system is selected between about 10 and 1000 Hz.

18. In apparatus for determining the visco-elastic properties of specimens including fluids and/or a polymerizing mixture, especially of coagulating fluids such as blood or blood plasma, and their temporal changes, including an elastic oscillation system for containing said specimen as a part thereof, the natural resonant frequency of said system changing as said specimen properties change, the improvement characterized by:
means for reading out at least the changing frequency position of the resonant frequency of said oscillation system occurring as said specimen properties change for determining specimen elasticity changes.

19. In apparatus for determining the visco-elastic properties of specimens including fluids and/or a polymerizing mixture, especially of coagulating fluids such as blood or blood plasma, and their temporal changes, including an elastic oscillation system for containing said specimen as a part thereof, the natural resonant frequency of said system changing as said specimen properties change, the improvement characterized by:
means for simultaneously reading out changes in the amplitude and frequency position of the resonant frequency of said oscillation system as said specimen properties change for determining changes in at least the elasticity of said specimen.

20. In apparatus for determining the visco-elastic properties of specimens including fluids and/or a polymerizing mixture, especially of coagulating fluids such as blood or blood plasma, and their temporal changes, including an elastic oscillation system for containing said specimen as a part thereof, the natural resonant frequency of said system changing as said specimen properties change, the improvement characterized by:
means for detecting changes in the amplitude of the resonant frequency of said oscillation system as said specimen properties change, and
means responsive to said amplitude changes for reading out at least the changing frequency position of the resonant frequency of said oscillation system occurring as said specimen properties change for determining specimen elasticity changes.

21. In apparatus for determining the visco-elastic properties of specimens including fluids and/or a polymerizing mixture, especially of coagulating fluids such as blood or blood plasma, and their temporal changes, including an elastic oscillation system for containing said specimen as a part thereof, the natural resonant frequency of said system changing as said specimen properties change, the improvement characterized by:
means for stimulating said elastic oscillation system into oscillation by applying thereto an excitation signal varying in frequency so as to coincide at least momentarily with successive momentary resonant frequencies of said oscillation system resulting from said specimen property changes,
means for detecting changes in the amplitude of the resonant frequency of said oscillation system as said specimen properties change, and
means for monitoring at least the changing frequency position of the resonant frequency of said oscillation system occurring as said specimen properties change for determining specimen elasticity changes.

22. Apparatus as in claim 21 wherein said monitoring means is responsive to the amplitude changes for sensing and indicating said changing frequency position.

23. Apparatus as in claim 22 including means sensing the maxima of said amplitude changes for adjusting the excitation signal frequency toward the momentary resonant frequency of said oscillation system.

24. Apparatus as in claim 23 wherein said monitoring means includes recording means for recording said changing frequency on a time base.

25. Apparatus as in claim 23 or 24 including means for recording the amplitude maxima on a time base.

26. Apparatus as in claim 22 including means for cyclically varying the frequency of said excitation signal through a predetermined range of frequencies which includes the starting and subsequent resonant frequencies of said oscillation system.

27. Apparatus as in claim 26 wherein said monitoring means includes a recording means responsive to said amplitude changes and frequency varying means for producing successive amplitude versus time curves varying in height along both axes to reflect changes in viscosity and elasticity of the specimen.

* * * * *

UNITED STATES PATENT AND TRADEMARK OFFICE
CERTIFICATE OF CORRECTION

PATENT NO. : 4,341,111
DATED : July 27, 1982
INVENTOR(S) : Dieter Husar

It is certified that error appears in the above-identified patent and that said Letters Patent is hereby corrected as shown below:

ON THE TITLE PAGE, insert

-- (30) Foreign Application Priority Data

March 5, 1980      Germany...29 08 469      --.

Signed and Sealed this

Eighteenth Day of January 1983

[SEAL]

Attest:

GERALD J. MOSSINGHOFF

Attesting Officer      Commissioner of Patents and Trademarks

UNITED STATES PATENT AND TRADEMARK OFFICE
CERTIFICATE OF CORRECTION

PATENT NO. : 4,341,111
DATED : July 27, 1982
INVENTOR(S) : Dieter HUSAR

It is certified that error appears in the above—identified patent and that said Letters Patent is hereby corrected as shown below:

ON THE TITLE PAGE re Priority Data [Item 30]

"March 5, 1980 Germany ..29 08 469.3"

should read --March 5, 1979 Germany ..29 08 469.3--

Signed and Sealed this

Sixth Day of September 1983

[SEAL]

Attest:

GERALD J. MOSSINGHOFF

Attesting Officer    Commissioner of Patents and Trademarks